United States Patent [19]

Maget

[11] Patent Number: 4,886,514

[45] Date of Patent: Dec. 12, 1989

[54] ELECTROCHEMICALLY DRIVEN DRUG DISPENSER

[75] Inventor: Henri J. R. Maget, La Jolla, Calif.

[73] Assignee: IVAC Corporation, San Diego, Calif.

[21] Appl. No.: 318,488

[22] Filed: Mar. 2, 1989

Related U.S. Application Data

[63] Continuation of Ser. No. 46,937, May 5, 1987, abandoned, which is a continuation-in-part of Ser. No. 729,860, May 2, 1985, abandoned.

[51] Int. Cl.[4] ............................................... A61K 9/22
[52] U.S. Cl. ................................. 604/891.1; 604/20; 604/96
[58] Field of Search .............. 604/890.1, 891.1, 892.2, 604/19, 20, 31, 67, 93, 95, 96–100, 131

[56] References Cited

U.S. PATENT DOCUMENTS

| | | | |
|---|---|---|---|
| 3,894,538 | 7/1975 | Richter | 204/301 |
| 3,995,632 | 12/1976 | Nakano et al. | 604/890.1 |
| 4,140,122 | 2/1979 | Kühll et al. | 604/890.1 |
| 4,235,236 | 11/1980 | Theeuwes | 604/892 |
| 4,340,048 | 7/1982 | Eckenhoff . | |
| 4,402,817 | 9/1983 | Maget | 204/301 |
| 4,486,190 | 12/1984 | Reinicke | 604/891.1 |
| 4,714,462 | 12/1987 | DiDomenico | 604/67 |
| 4,718,893 | 1/1988 | Dormon et al. | 604/891.1 |

OTHER PUBLICATIONS

Electroosmotic Pump for the Uniform, Regulated or Controlled Release of Drugs, G. Luft, D. Kuhl, G. J. Richter.

Primary Examiner—C. Fred Rosenbaum
Assistant Examiner—Sharon Rose
Attorney, Agent, or Firm—Fulwider, Patton, Lee & Utecht

[57] ABSTRACT

An electrochemically driven drug dispenser for dispensing a drug at a controlled rate. The drug dispenser includes an electrochemical pump which pumps an electrochemically active fluid from a first compartment through a membrane into a second compartment. As the fluid enters the second compartment it exerts pressure on a diaphragm separating the second compartment from a chamber containing a drug to be administered. As the pressure increases, the drug is expelled. In the absence of any pumping action, the fluid moves between the two compartments by diffusion through the membrane at a rate which is characteristic of the membrane and determined by any pressure difference between the two compartments. The pumping rate is determined by the magnitude of an electric current applied to the pump, and by varying the pumping rate with reference to the diffusion rate any of a variety drug administration rates can be implemented. A pressure sensor may be included in the pump for more precise control of the pumping rate. The membrane may be fabricated of electrolytic and non-electrolytic portions so that a desired diffusion rate can be achieved.

16 Claims, 2 Drawing Sheets

ELECTROCHEMICALLY DRIVEN DRUG DISPENSER

This application is a continuation of application Ser. No. 046,937 filed May 5, 1987, now abandoned, which is in turn a continuation-in-part of application Ser. No. 729,860, filed May 2, 1985, abandoned.

BACKGROUND OF THE INVENTION

This invention relates generally to devices for the infusion of drugs into the human body, and, more particularly, to pump driven devices for the highly accurate infusion of small quantities of drugs.

The administration of drugs to a patient can be accomplished through a variety of methods, including gravity, mechanical pumps, pressurized gases and osmosis. A gravity dispenser utilizes the force of gravity to dispense a drug suspended above the patient. The delivery rate of the drug is adjusted by means of the pressure head, the height of the drug above the patient, and by a restriction of the outlet line leading to the patient. However, the delivery rate of the gravity dispenser is difficult to control accurately because of changes in the height of the drug as it is dispensed to the patient, changes in the posture of the patient and even variations in the back pressure of the patient's blood. More importantly, however, the patient is greatly restricted in mobility, since the drug must be constantly suspended in a container above the patient. A typical controller for adjusting the delivery rate of the gravity force dispenser is disclosed in U.S. Pat. No. 4,300,552 to Cannon.

Other methods for administering drugs eliminate the need for suspending the drug above the patient and, therefore, greatly improve the mobility of the patient. Mechanical pump dispensers generally consist of an electrically driven mechanical pump. These pumps provide accurate control of the delivery rate of the drug, but incorporate moving parts, which can wear out and break down. These pumps also consume relatively large amounts of power. Other dispensers employ a pressurized gas to administer the drug to the patient. Generally, these dispensers are large and bulky, and not easily portable. Furthermore, regulation of the delivery rate is often difficult. Typical pressurized gas dispensers are disclosed in U.S. Pat. No. 2,766,907 to Wallace, Jr. and U.S. Pat. No. 4,237,881 to Beigler et al.

Osmosis driven dispensers depend on solutes that exhibit an osmotic pressure gradient against water. The delivery rate provided by these dispensers is determined by the type of solute used and, therefore, the delivery rate cannot be varied during operation. Representative osmotic dispensers are disclosed in U.S. Pat. No. 3,995,632 to Nakano et al., U.S. Pat. No. 4,034,756 to Higuchi et al. and U.S. Pat. No. 4,439,196 to Higuchi. Electrically controlled osmotic dispensers are disclosed in U.S. Pat. No. 3,923,426 to Theeuwes and U.S. Pat. No. 3,894,538 to Richter.

Many patients require a continuous infusion of small quantities of drugs over a period which may be many hours or even several days in duration. Such drugs sometimes must be dispensed at constant, precisely-controlled rates; in other cases, the drugs must be dispensed in a cyclical, pulsating fashion, or at a controlled variable rate. Accordingly, there is a need for a portable, implantable drug dispenser that can accurately dispense small quantities of drugs at a desired rate extending over a relatively long period of time.

SUMMARY OF THE INVENTION

The present invention provides an electrochemically driven drug dispenser wherein an electrochemical pump provides a controllable source of varying pressure for accurately delivering a small quantity of a drug at a desired delivery rate over an extended period of time. A drug dispenser according to the invention is implantable, has no moving parts, and achieves the desired delivery rate by means of an electronic controller.

An electrochemical pump is a pump in which an electrochemically active fluid is pumped from one compartment across an electrolytic membrane into another compartment by an electric current. The fluid is ionized in the one compartment and the ions are propelled through the membrane and are recombined into fluid in the other compartment.

A drug dispenser according to the invention includes a container, separating means dividing the container into a drug chamber and a pump chamber, an electrochemically active fluid in the pump chamber, an electrolytic membrane dividing the pump chamber into first and second compartments, electrodes on opposing sides of the membrane, and means to provide an electric current to the electrodes. The electric current pumps the fluid from one compartment to the other at a rate determined by the magnitude of the current. As the fluid flows into the second compartment it exerts pressure on the separating means to discharge a drug from the drug chamber. Control means varies the magnitude of the current to discharge the drug at a predetermined rate.

In the absence of any current, the fluid diffuses through the membrane at a characteristic rate of diffusion proportional to any difference between the pressure of the fluid in one compartment and the pressure of the fluid in the other. The control means varies the current with reference to this diffusion rate such that the net rate of flow of the fluid, being equal to an algebraic sum of the pumping rate and the diffusion rate, discharges the drug at the predetermined rate.

The drug may be discharged through a delivery port and check valve, a permeable membrane, or the like. The fluid may comprise hydrogen or oxygen or the like. The separating means may comprise a flexible diaphragm, a sliding wall, or some other device through which pressure can be communicated from the pump chamber to the drug chamber.

The control means may linearly vary the current at a rate proportional to the diffusion rate to discharge the drug at a constant rate, or the current may be intermittently varied to deliver the drug at a pulsating rate. Pressure sensing means may be included in one of the compartments to sense the pressure for more precise control. The membrane may include a non-electrolytic portion which may be selected according to its diffusion characteristics.

It will be appreciated from the foregoing that a drug dispenser according to the invention can achieve accurate delivery rates at low dosage levels over an extended period of time in a portable, implantable unit. A complex delivery schedule can readily be implemented by electronically varying the pumping current. Other aspects and advantages of the invention will become apparent from the following detailed description, taken together with the accompanying drawings which illustrate by way of example the principles of the invention.

DESCRIPTION OF THE PREFERRED EMBODIMENTS

As shown in the exemplary drawings, the invention is embodied in a novel electrochemically driven drug dispenser. Many patients require infusion of small quantities of drugs over an extended period of time and, therefore, a portable, small, implantable, accurate and reliable drug dispenser has been required. Numerous present-day drug dispensers are designed for in-hospital use and are not portable. Others are portable but may not provide accurate control of the drug delivery rate or may have moving parts that can wear out and break down. Still others may have relatively large power requirements.

In accordance with the invention, an electrochemical pump provides a variable pressure source for accurate control of a drug delivery rate with no moving parts and with little power consumption. Moreover, the pump can be miniaturized for implantation. The electrochemical pump described in U.S. Pat. No. 4,402,817 to the present inventor is typical of such a pump.

Figure 1:
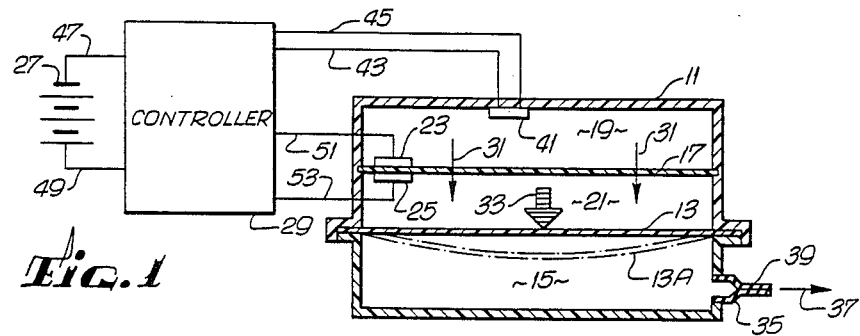
FIG. 1 is a sectional view of a drug dispenser according to the invention.

FIG. 1 illustrates a preferred embodiment of an electrochemically driven drug dispenser according to the invention. The dispenser comprises a gas-tight container 11 with separating means such as a flexible expansible diaphragm 13 disposed in the container 11 and defining therein a drug chamber 15 for receiving a drug and a pump chamber separated from the drug chamber 15 by the separating means. An electrochemically active fluid such as hydrogen or oxygen is disposed in the pump chamber.

An electrolytic membrane 17 is disposed in the pump chamber and defines therein first and second compartments 19 and 21, respectively. The diaphragm 13 is comprised in a side of the second compartment 21. The membrane 17 is characterized by a rate of diffusion of the fluid therethrough from one of the compartments to the other, the diffusion rate being proportional to any difference between the pressure of the fluid in one compartment and the pressure of the fluid in the other compartment.

First and second electrodes 23 and 25 are disposed in the first and second compartments 19 and 21, respectively, on opposing sides of the membrane 17. Means 27 provides an electric current to the electrodes 23 and 25 to pump the fluid from one compartment to the other at a rate determined by the magnitude of the current, the net rate of flow of the fluid from one compartment to the other being equal to an algebraic sum of the pumping rate and the diffusion rate.

Control means 29 varies the magnitude of the current with reference to the diffusion rate to cause the fluid to flow from the first compartment 19 to the second compartment 21 as indicated by arrows 31 and exert pressure on the diaphragm 13 as indicated by an arrow 33 to discharge a drug from the drug chamber 15 at a predetermined rate. As the fluid flows into the second compartment 21, the diaphragm 13 expands into the drug chamber 15 toward a position 13A, squeezing the drug out through a delivery port 35 as indicated by an arrow 37. A check valve 39 may be provided to prevent any reverse flow of drug or contaminants back into the chamber 15.

The control means 29 may linearly vary the magnitude of the current at a rate proportional to the diffusion rate, causing the fluid to flow from the first compartment 19 to the second compartment 21 at a constant net rate and thereby discharging the drug at a constant rate. Or the control means 29 may intermittently vary the magnitude of the current according to the diffusion rate, causing the fluid to flow intermittently from the first compartment 19 to the second compartment 21 and thereby discharging the drug at a pulsating rate.

The drug dispenser may be supplied with a drug already disposed in the drug chamber 15 or the drug may be installed in the field, for example by running the electrochemical pump in reverse to draw the drug into the drug chamber 15.

Pressure sensing means 41 may be provided to sense the pressure of the fluid in one of the compartments. The sensing means 41 is shown disposed in the first compartment 19, but it will be apparent that the sensing means 41 could be disposed in the second compartment 21 instead. The control means 29 is responsive to the sensing means 41 to vary the magnitude of the current with reference to the sensed pressure of the fluid so as to more precisely control the rate of discharge of the drug.

The pressure sensing means 41 may comprise, for example, a silicon piezoelectric pressure sensor such as a Motorola type MPX200 or a Sensym series SX or SPX. The sensing means 41 is connected to the control means 29 by conductors 43 and 45.

The current providing means 27 may comprise a dry cell or most any other source of electric power. The means 27 is connected to the control means 29 by conductors 47 and 49. The first and second electrodes 23 and 25 are connected to the control means 29 by conductors 51 and 53, respectively.

Figure 2:
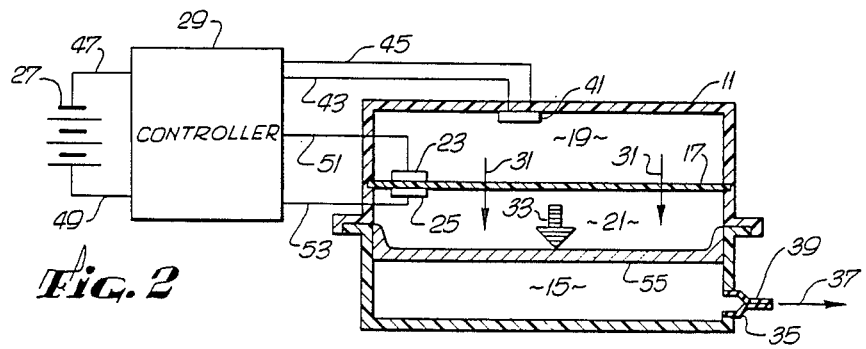
FIG. 2 is a sectional view of a drug dispenser similar to that shown in FIG. 1 but having a sliding wall rather than a flexible diaphragm.
Figure 3:
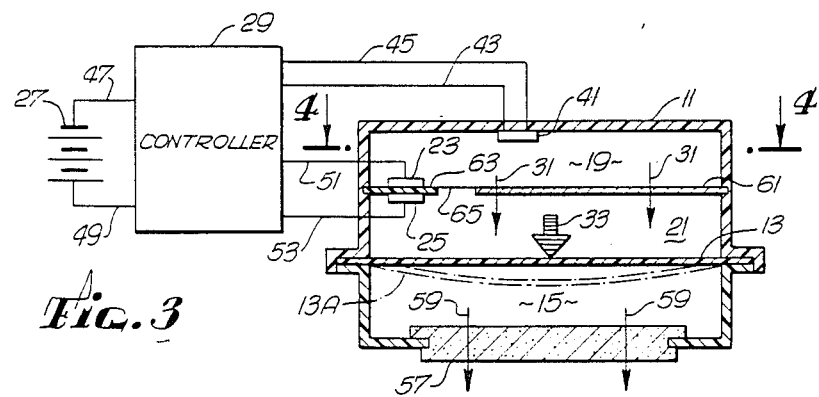
FIG. 3 is a sectional view of a drug dispenser similar to that shown in FIG. 1 but having a permeable membrane rather than a delivery port for discharge of a drug and also including a dual membrane structure.

Alternate embodiments of a drug dispenser according to the invention are shown in FIGS. 2 and 3. Except as noted, these embodiments are similar to the embodiment of FIG. 1, and the same reference numerals are used to identify components which are unchanged from one embodiment to the other.

In the embodiment shown in FIG. 2, the separating means comprises a sliding wall 55 rather than the diaphragm 13. The wall 55 slides into the drug chamber 15 under the influence of pressure from the fluid flowing into the second compartment 21, squeezing the drug out through the delivery port 35.

The embodiment shown in FIG. 3 comprises a permeable membrane 57 included in a side of the drug chamber 15 through which the drug can be discharged from the drug chamber 15 as indicated by arrows 59. The membrane 57 may be a drug-specific membrane which provides a fixed pressure drop for the drug and prevents any reverse flow of the drug or of any contaminants back into the drug chamber 15.

Figure 4:
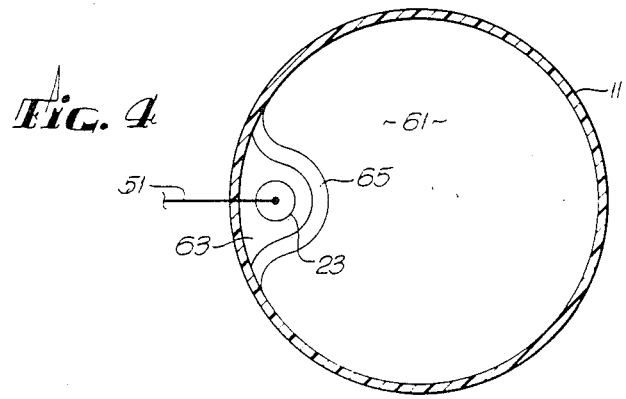
FIG. 4 is a sectional view taken along the line 4—4 of FIG. 3 and showing the dual membrane structure.

The diffusion rate which characterizes the membrane 17 is largely determined by the material from which the membrane 17 is fabricated. Only a few substances can be used to make a practical electrolytic membrane and for some applications none of these has an optimum diffusion rate. To obtain a desired diffusion rate other than that which can be obtained from available electrolytic membrane substances, the membrane can be made in two portions—a non-electrolytic portion 61 and an electrolytic portion 63, as shown in FIGS. 3 and 4.

The non-electrolytic portion 61 is characterized by a first rate of diffusion of the fluid therethrough from one of the compartments to the other, and the electrolytic portion 63 is characterized by a second rate of diffusion of the fluid therethrough. The two portions 61 and 63 are connected by a joining means 65.

The non-electrolytic portion 61 may be much larger in surface area than the electrolytic portion 63, with the result that most of the diffusion takes place through the non-electrolytic portion and the first diffusion rate dominates to such an extent that the second may be ignored by the control means 29. Or, the control means 29 may regulate the electric current with reference to both diffusion rates if the effects of both are significant.

The non-electrolytic portion of the membrane may comprise many different substances, among them silicone film (which has a relatively high diffusion rate) and teflon (which has a somewhat lower rate).

The simple construction of the drug dispenser provides a device which has no moving parts and is highly reliable. The gas-tight container 11 can be composed of any material impervious to gas, such as metal, glass or plastic. The electrolytic membrane 17 or the electrolytic portion 63 of a dual-portion membrane is preferably a solid-type membrane, preferably an ion exchange membrane, and can be composed of any material containing dissociated functional groups capable of transporting either cations or anions. The electrodes 23 and 25 can be constructed of any material that is electrically conductive and acts as a catalyst in converting the fluid molecules in the first compartment 19 to ions and reconverting those ions to fluid molecules in the second compartment 21 in response to a current applied to the electrodes 23 and 25.

The electrochemically active fluid can comprise any reduction/oxidation fluid that is electrochemically reversibly active so as to react at the electrode 23 to produce ions, which will then migrate through the electrolytic membrane 17 and be reconverted at the electrode 25 into a molecular state. Hydrogen gas is one suitable example. At the electrode 23 an anodic reaction occurs, represented by the equation:

$$H_2 \rightarrow 2H^+ + 2e^-$$

The hydrogen gas molecules in the first compartment 19 are therefore converted into ions which move through the electrolytic membrane 17. At the electrode 25 a cathodic reaction occurs, represented by the equation:

$$2H^+ + 2e^- \rightarrow H_2$$

The hydrogen gas ions are therefore reconverted into hydrogen gas molecules and released into the second compartment 21. The net result is a flow of hydrogen gas from the first compartment 19 to the second compartment 21.

Other suitable fluids which may be used include, for example, such gases as oxygen or air.

Before a drug can be administered, the fluid must be in the first compartment 19. If some of the fluid has diffused through the membrane 17 into the second compartment 21, it may be necessary to run the pump in reverse so as to pump the fluid from the second compartment 21 into the first compartment 19. Moreover, once the fluid is all, or nearly all, in the first compartment 19 it will be necessary to continue to run the pump in reverse to keep the fluid in the first compartment 19. Otherwise the fluid will diffuse through the membrane 17 back into the second compartment 21 until the pressures in the two compartments 19 and 21 are equal.

To prepare the device for use in minimum time, a relatively large reverse current can be provided by a power source other than the means 27 to rapidly pump all the fluid into the first compartment 19. The drug chamber 15 can then be filled with a drug, or the drug can be sucked in while the fluid is being pumped from the second compartment 21 into the first compartment 19.

Once the device has been prepared for use, the quantity of fluid in the first compartment 19 can be maintained constant by running the pump at a rate equal and opposite to the diffusion rate. To begin administering a drug, it is only necessary to reduce the reverse pumping rate so that the diffusion rate in the forward direction exceeds the reverse pumping rate by an amount equal to the desired rate of drug administration.

As the fluid flows into the second compartment 21, the volume of that compartment increases and the volume of the drug chamber 15 correspondingly decreases as the drug is expelled. During this process the pressure in the second compartment 21 remains nearly constant. However, the amount of fluid in the first compartment 19 is steadily decreasing, resulting in a steadily decreasing pressure in the first compartment 19. This in turn leads to a steadily decreasing diffusion rate from the first compartment 19 into the second compartment 21. Accordingly, the current must be reduced to effect a reduction in the reverse pumping rate which then offsets the decreased diffusion rate and maintains a constant net flow rate of fluid into the second compartment 21. This reduction in current is proportional to the reduction in diffusion through the membrane 17. The overall result is that the reverse current drawn by the pump must be linearly reduced over time by the control means 29.

The linear reduction in reverse current will continue until the pressure differential between the two compartments is zero, at which time the current flow is also zero. Forward pumping is then begun by reversing the polarity of the current. As the pressure in the first compartment 19 is reduced below that of the constant pressure being maintained in the second compartment 21, the diffusion will also reverse direction, being now from the second compartment 21 to the first compartment 19.

The diffusion rate will linearly increase, as must the current required to maintain the constant pressure in the second compartment 21 until the diffusion rate from the second compartment 21 to the first compartment 19 equals the maximum pumping rate in the forward direction. At this point, the drug chamber 15 must be refilled.

In most cases, diffusion rates are very predictable, the rate being dependent on such variables as the type of membrane materials, the membrane thickness and the type of fluid used. Therefore, the diffusion rate can be readily determined, which in turn allows for a straightforward and highly accurate calculation of the current required for a specific drug delivery rate. The net flow of the fluid through the membrane 17, including both the pump flow and the diffusion flow, can be expressed by the relation:

$$R = \left[ \frac{P_l \cdot S_m \cdot (P_u - P_L)}{d} + K \cdot I \right] \frac{1}{P_L} \quad (1)$$

where
$R$ = the net flow rate,
$P_e$ = the permeability of the membrane,
$d$ = the membrane thickness,
$K$ = the pump flow rate constant,
$I$ = the electrical current,
$P_u$ = the pressure in the first (upper) compartment,
$P_L$ = the pressure in the second (lower) compartment,
$S_m$ = the membrane area,
$V_u$ = the volume of the first compartment, and
$V_L$ = the volume of the second compartment.

If a constant delivery rate is desired, the pressure in the second compartment ($P_l$) must remain constant. If a fixed first compartment volume $V_u$ is used, then:

$$P_L \cdot V_L(t) + P_u(t) \cdot V_u = \text{constant} \quad (2)$$

where only $V_L$ and $P_u$ are functions of time. Taking the derivative with respect to time:

$$P_L \cdot \frac{dV_L(*)}{dt} + V_u \cdot \frac{dP_u(t)}{dt} = 0 \quad (3)$$

But $$\frac{dV_L(t)}{dt}$$

is merely $R$, the net flow rate through the membrane 17.
Substituting $R$ and rearranging equation (3):

$$-\frac{dP_u(t)}{dt} = \frac{P_L \cdot R}{V_u} \quad (4)$$

Integrating:

$$P_u(o) - P_u(t) = \frac{P_L \cdot R \cdot t}{V_u} \quad (5)$$

Combining equations (1) and (5) yields the expression for the required current as a function of time:

$$I = \frac{R \cdot P_L}{k} + \frac{P_l \cdot S_m}{K \cdot d} \left[ P_L \left( \frac{R \cdot t}{V_u} + 1 \right) - P_u(o) \right] \quad (6)$$

Inserting the known constants into equation (6) yields a first order linear equation as a function of time. Such an equation can be implemented quite easily in any simple digital or analog controller.

Figure 5A:
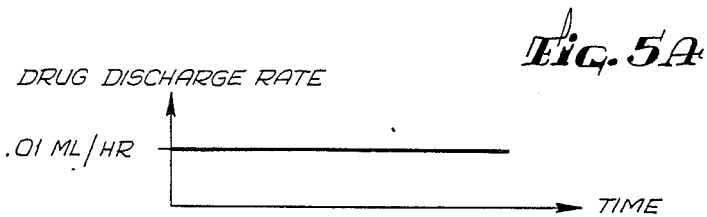
FIG. 5A is a graph showing a constant drug discharge rate.

For example, assume a desired drug delivery rate of 0.01 milliliters per hour as shown graphically in FIG. 5A. If the drug dispenser uses hydrogen as the electrochemically active fluid and has the following characteristics:

a membrane 17 characterized by:
surface area $S_m = 1.0$ cm$^2$
thickness $d = 0.025$ cm
hydrogen permeability
$P_e = 6.25 \times 10^{-3}$ cm$^3$—cm/cm$^2$·sec. atmos.
desired pressure in second compartment = 1.1 atmos.
volume of first compartment = 1 milliliter
initial pressure of hydrogen = $P_u = 1.354$ atmos.

Equation (6) can then be evaluated with the following result:

current $I = (2.2t - 26.4)$ microamps

Figure 5B:
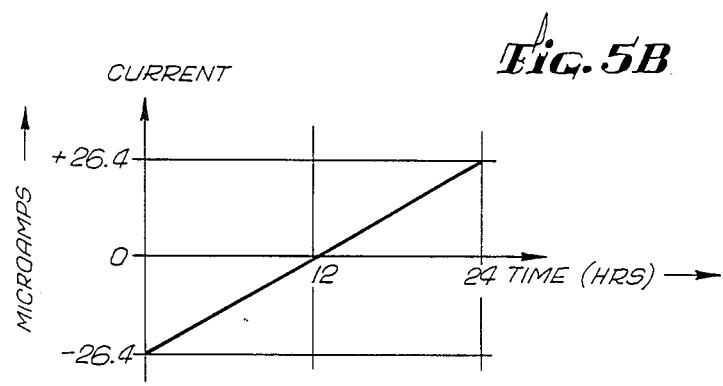
FIG. 5B is a graph showing the electric current, as a function of time, required to produce the drug discharge rate shown in FIG. 5A.

A linear variation of the current from $-26.4$ microamps to $+26.4$ microamps in 24 hours, as shown graphically in FIG. 5B, is therefore required to maintain a constant 0.01 ml/hr rate of drug administration for a 24 hour period.

Figure 6A:
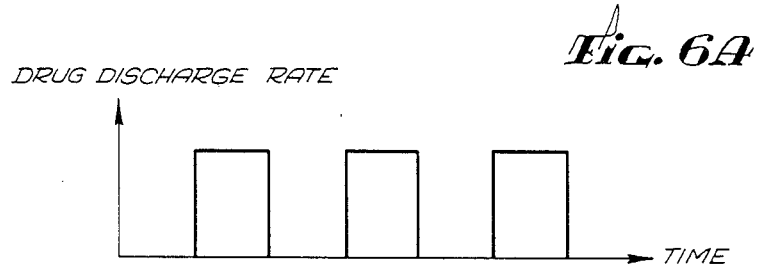
FIG. 6A is a graph showing a pulsating drug discharge rate.
Figure 6B:
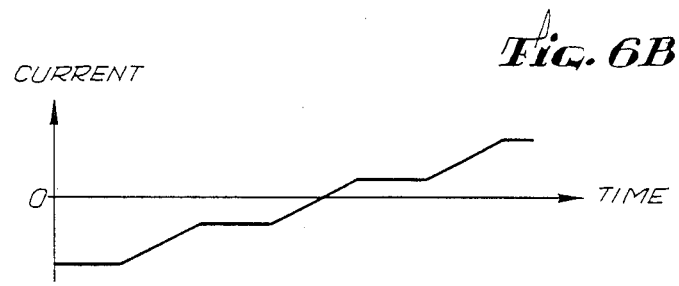
FIG. 6B is a graph showing the electric current, as a function of time, required to produce the drug discharge rate shown in FIG. 6A.

Similar calculations may be performed to achieve other rates of drug administration. For example, it may be desired to administer a drug at a pulsating rate wherein the drug is administered at a constant rate, say 0.1 ml/hr, for one hour, then is shut off for one hour, then is again administered at a constant rate for an hour, and so forth, as shown graphically by a square wave pattern in FIG. 6A. The current flow required to achieve the pulsating drug administration rate of FIG. 6A is shown graphically in FIG. 6B to comprise a constant current flow, equal and opposite to the diffusion rate, during periods when the flow of the drug is to be shut off, and a linearly increasing current flow, analogous to the linearly increasing current flow depicted in FIG. 5B, during periods when drug flow at a constant rate is desired.

A drug dispenser according to the invention provides a means to administer a drug at a low, precisely controlled rate over an extended period of time. The dispenser is completely self-contained and may conveniently be implanted or carried with the patient as desired. By utilizing a dual membrane structure wherein one portion of the membrane is non-electrolytic and by judicious choice of membrane material, a dispenser having a wide range of diffusion rates can be fabricated. For a dispenser having a given diffusion rate, any of a plurality of drug administration rates may be selected simply by replacing or reprogramming the current control means.

Although certain specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

I claim:
1. An electrochemically driven drug dispenser comprising:

a container;

separating means disposed in the container and defining therein a drug chamber for receiving a drug and a gas pressure pump chamber separated from the drug chamber by the separating means;

an electrochemically active gas disposed in the pump chamber;

a membrane disposed in the pump chamber and defining therein a first pressure containment compartment and a second compartment, the separating means comprised in a side of the second compartment, the membrane comprising a non-electrolytic portion and an electrolytic portion, the non-electrolytic portion characterized by a first rate of diffusion of the gas therethrough from one of the components to the other, the diffusion rate being proportional to any difference between the pressure of the gas in one compartment and the pressure of the gas in the other compartment;

first and second electrodes disposed in the first and second compartments, respectively, on opposing sides of the electrolytic portion of the member, the gas being electrochemically reversibly active so as to enter into an anodic reaction at one electrode in which anodic reaction molecules of the gas are converted into ions that are transportable through the membrane and a cathodic reaction at the other electrode in which cathodic reaction ions are reconverted back into molecules of the gas;

means to provide an electric current to the electrodes, the current being operative to transport the ions through the electrolytic portion of the membrane whereby the gas is effectively pumped from one compartment to the other at a pumping rate determined by the polarity and magnitude of the current, the net rate of flow of the gas from one compartment to the other being equal to an algebraic sum of the pumping rate and the diffusion rate; and first control means to vary the magnitude and direction of the current with reference to the first diffusion rate to cause the gas to flow from the first compartment to the second sufficient to exert pressure on the separating means to discharge a drug from the chamber at a predetermined rate.

2. A drug dispenser according to claim 1 and further comprising a drug disposed in the drug chamber.

3. A drug dispenser according to claim 1 and further comprising a delivery port and a check valve through which a drug can be discharged from the drug chamber.

4. A drug dispenser according to claim 1 and further comprising a permeable membrane through which a drug can be discharged from the drug chamber.

5. A drug dispenser according to claim 1 wherein the gas comprises hydrogen.

6. A drug dispenser according to claim 1 wherein the gas comprises oxygen.

7. A drug dispenser according to claim 1 wherein the separating means comprises a flexible diaphragm.

8. A drug dispenser according to claim 1 wherein the separating means comprises a sliding wall.

9. A drug dispenser according to claim 1 wherein the control means linearly varies the magnitude to the current at a rate proportional to the diffusion rate, causing the gas to flow from the first compartment to the second at a constant net rate and thereby discharging the drug at a constant rate.

10. A drug dispenser according to claim 1 wherein the control means intermittently varies the magnitude of the current according to the diffusion rate, causing the gas to flow intermittently from the first compartment to the second and thereby discharging the drug at a pulsating rate.

11. A drug dispenser according to claim 1 wherein the electrolytic portion of the membrane is characterized by a second rate of diffusion of the gas therethrough from one of the compartments to the other and wherein the control means varies the magnitude of the current with reference to both diffusion rates.

12. A drug dispenser according to claim 11 wherein the control means linearly varies the magnitude of the current at a rate proportional to both diffusion rates, causing the gas to flow from the first compartment to the second at a constant net rate and thereby discharging the drug at a constant rate.

13. A drug dispenser according to claim 11 wherein the control means intermittently varies the magnitude of the current according to both diffusion rates, causing the gas to flow intermittently from the first compartment to the second and thereby discharging the drug at a pulsating rate.

14. An electrochemically driven drug dispenser comprising:

a container;

separating means disposed in the container and defining therein a drug chamber for receiving a drug and a gas pressure pump chamber separated from the drug chamber by the separating means;

an electrochemically active gas disposed in the pump chamber;

a membrane disposed in the pump chamber and defining therein a first pressure containment compartment and a second compartment, the separating means comprised in a side of the second compartment, the membrane comprising a non-electrolytic portion and an electorlytic portion, the non-electrolytic portion characterized by a first rate of diffusion of the gas therethrough from one of the compartments to the other, the diffusion rate being proportional to any difference between the pressure of the gas in one compartment and the pressure of the gas in the other compartment, and the electrolytic portion characterized by a second rate of diffusion of the gas therethrough from one of the compartments to the other;

first and second electrodes disposed in the first and second compartments, respectively, on opposing sides of the electrolytic portion of the membrane, the gas being electrochemically reversibly active so as to enter into an anodic reaction at one electrode in which anodic reaction molecules of the gas are converted into ions that are transportable through the membrane and a cathodic reaction at the other electrode in which cathodic reaction ions are reconverted back into molecules of the gas;

pressure sensing means to sense the pressure of the gas in one of the compartments;

means to provide an electric current to the electrodes, the current being operative to transport the ions through the electrolytic portion of the membrane whereby the gas is effectively pumped from one compartment to the other at a pumping rate determined by the polarity and magnitude of the current, the net rate of flow of the gas from one compartment to the other being equal to an algebraic sum of the pumping rate and the diffusion rate; and control means, responsive to the pressure sensing means to vary the magnitude and direction of the current with reference to the pressure of the gas to cause the gas to flow from the first compartment to the second and sufficient to exert pressure on the separating means to discharge a drug from the drug chamber at a predetermined rate.

15. A drug dispenser according to claim 14 wherein the control means linearly varies the magnitude of the current at a rate proportional to the sensed pressure, causing the gas to flow from the first compartment to the second at a constant net rate and thereby discharging the drug at a constant rate.

16. A drug dispenser according to claim 14 wherein the control means intermittently varies the magnitude of the current according to the sensed pressure, causing the gas to flow intermittently from the first compartment to the second and thereby discharging the drug at pulsating rate.

* * * * *